US010278345B2

(12) United States Patent
Arnold et al.

(10) Patent No.: US 10,278,345 B2
(45) Date of Patent: *May 7, 2019

(54) METHODS AND DEVICES FOR CREATING DOUBLED HAPLOID EMBRYOS USING OIL MATRICES

(71) Applicant: PIONEER HI-BRED INTERNATIONAL, INC., Johnston, IA (US)

(72) Inventors: Randal Arnold, Ankeny, IA (US); Roberto Barreiro, Honolulu, HI (US); Matthew Paul Cope, Johnston, IA (US); Clifford P Hunter, Mililani, HI (US); Justin Andrew Schares, Ames, IA (US); Xinli Emily Wu, Johnston, IA (US); Yue Yun, Johnston, IA (US)

(73) Assignee: PIONEER HI-BRED INTERNATIONAL, INC. IA (US)

( * ) Notice: Subject to any disclaimer, the term of this patent is extended or adjusted under 35 U.S.C. 154(b) by 225 days.

This patent is subject to a terminal disclaimer.

(21) Appl. No.: 15/248,010

(22) Filed: Aug. 26, 2016

(65) Prior Publication Data

US 2016/0360716 A1 Dec. 15, 2016

Related U.S. Application Data

(63) Continuation of application No. 14/793,689, filed on Jul. 7, 2015, now Pat. No. 9,706,723, and a continuation-in-part of application No. 14/473,114, filed on Aug. 29, 2014, and a continuation-in-part of application No. 14/473,183, filed on Aug. 29, 2014, now Pat. No. 9,078,427.

(51) Int. Cl.
*A01H 4/00* (2006.01)
*A01H 1/08* (2006.01)
*C12Q 1/6806* (2018.01)
*C12N 15/82* (2006.01)
*A01C 1/02* (2006.01)
*A01C 1/06* (2006.01)
*A01N 3/00* (2006.01)
*C12Q 1/6895* (2018.01)

(52) U.S. Cl.
CPC ............ *A01H 4/006* (2013.01); *A01C 1/025* (2013.01); *A01C 1/06* (2013.01); *A01H 1/08* (2013.01); *A01N 3/00* (2013.01); *C12N 15/8205* (2013.01); *C12Q 1/6806* (2013.01); *C12Q 1/6895* (2013.01); *C12Q 2600/13* (2013.01); *C12Q 2600/156* (2013.01); *C12Q 2600/158* (2013.01)

(58) Field of Classification Search
None
See application file for complete search history.

(56) References Cited

U.S. PATENT DOCUMENTS

| | | |
|---|---|---|
| 5,138,793 A | 8/1992 | Florin et al. |
| 5,565,335 A | 10/1996 | Capon et al. |
| 5,943,821 A | 8/1999 | Ducos et al. |
| 6,145,247 A | 11/2000 | McKinnis |
| 6,180,405 B1 | 1/2001 | Aitken-Christie et al. |
| 6,455,312 B1 | 9/2002 | Gray et al. |
| 6,627,441 B1 | 9/2003 | Attree |
| 6,677,154 B2 | 1/2004 | Gielis et al. |
| 6,689,609 B1 | 2/2004 | Fan et al. |
| 6,695,765 B1 | 2/2004 | Beebe et al. |
| 6,905,843 B1 | 6/2005 | Endo et al. |
| 7,326,826 B2 | 2/2008 | Gray et al. |
| 7,665,243 B2 | 2/2010 | Nehra et al. |
| 7,935,529 B2 | 5/2011 | Davis et al. |
| 8,119,342 B2 | 2/2012 | Van Dun |
| 8,216,840 B2 | 7/2012 | Jamruszka |
| 8,216,841 B2 | 7/2012 | Nehra et al. |
| 8,313,946 B2 | 11/2012 | Becwar et al. |
| 8,321,191 B2 | 11/2012 | Jones, III |
| 8,404,930 B2 | 3/2013 | Wu et al. |
| 8,452,460 B2 | 5/2013 | Aidun |
| 8,535,877 B2 | 9/2013 | Cope et al. |
| 8,859,846 B2 | 10/2014 | Barton et al. |
| 8,865,971 B2 | 10/2014 | Zhao et al. |
| 9,404,930 B2 | 8/2016 | Grabulovski et al. |
| 2002/0174454 A1 | 11/2002 | Lopez-Molina et al. |
| 2002/0188965 A1 | 12/2002 | Zhao |
| 2003/0005489 A1 | 1/2003 | Gray et al. |
| 2005/0050592 A1 | 3/2005 | Gray et al. |
| 2005/0186655 A1 | 8/2005 | Endo et al. |

(Continued)

FOREIGN PATENT DOCUMENTS

| | | |
|---|---|---|
| AU | 1994/77169 A | 5/1995 |
| AU | 703582 B2 | 3/1999 |

(Continued)

OTHER PUBLICATIONS

King et al (Biotechnology (1989) 7:1037-1042).*
Yamakawa et al (Agric. Bio. Chem (1983) 47: 2185-2191).*
Mroginski, et al.; "A cryopreservation protocol for immature zygotic embryos of species of Ilex (Aquifoliaceae)"; Biocell (2008) 32(1):33-39.
Nadarajan, et al.; "Optimization of cryopreservation for sterculia cordata zygotic embryos using vitrification techniques"; Journal of Tropical Forest Science (2007) 19(2):79-85.

(Continued)

*Primary Examiner* — Matthew R Keogh

(57) ABSTRACT

Methods for preserving viability of plant tissues such as plant embryos are provided herein. Also included are methods for storing genomic DNA and/or molecular marker assay materials in an oil bilayer as part of a high-throughput molecular characterization system. Moreover, plant embryos may be treated while in an oil matrix. The treatment may include chromosome doubling, *Agrobacterium*-mediated transformation, or herbicide selection as part of an embryo rescue process.

19 Claims, No Drawings

(56) References Cited

U.S. PATENT DOCUMENTS

| | | |
|---|---|---|
| 2005/0202573 A1 | 9/2005 | Koyata |
| 2005/0246790 A1 | 11/2005 | Gray et al. |
| 2006/0041959 A1 | 2/2006 | Hooykaas et al. |
| 2007/0204366 A1 | 8/2007 | Depperman |
| 2008/0131924 A1 | 6/2008 | Cope |
| 2008/0216191 A1 | 9/2008 | Barton et al. |
| 2009/0215060 A1 | 8/2009 | Deppermann et al. |
| 2010/0167376 A1 | 7/2010 | Hogan et al. |
| 2010/0184152 A1 | 7/2010 | Sandler et al. |
| 2012/0202289 A1 | 8/2012 | Aidun |
| 2012/0276634 A1 | 11/2012 | Clark et al. |
| 2013/0065762 A1 | 3/2013 | Stoller et al. |
| 2013/0210006 A1 | 8/2013 | Rapier et al. |
| 2015/0191771 A1 | 7/2015 | Bullock et al. |

FOREIGN PATENT DOCUMENTS

| | | |
|---|---|---|
| AU | 750133 B2 | 2/2000 |
| AU | 765886 B2 | 3/2000 |
| CA | 2296362 A1 | 11/1999 |
| CA | 2276003 A1 | 12/1999 |
| CA | 2322438 A1 | 12/1999 |
| CA | 2125410 C | 3/2000 |
| CM | 103657769 A | 3/2014 |
| CN | 101165174 A | 4/2008 |
| CN | 10057796 C | 1/2010 |
| CN | 102246959 A | 11/2011 |
| GB | 2091534 A | 8/1982 |
| ID | 201302434 A | 6/2013 |
| WO | 1989/05575 A1 | 6/1989 |
| WO | 1995/014373 A1 | 6/1995 |
| WO | 1998/37173 A2 | 8/1998 |
| WO | WO2002085104 A2 * | 4/2002 |
| WO | 02/085014 A2 | 10/2002 |
| WO | 2005/000471 A1 | 1/2005 |
| WO | 2005/030988 A1 | 4/2005 |
| WO | 2007/103786 A2 | 9/2007 |
| WO | 2011/019863 A1 | 2/2011 |
| WO | 2011/119763 A1 | 9/2011 |
| WO | 2012/011091 A2 | 1/2012 |
| WO | WO-2012011091 A2 * | 1/2012 |
| WO | 2013/119962 A1 | 8/2013 |
| WO | 2013/182646 A1 | 12/2013 |
| WO | 2014/071271 A1 | 5/2014 |
| WO | 2014/195199 A1 | 12/2014 |
| WO | 2015/104358 A1 | 7/2015 |

OTHER PUBLICATIONS

Nagano, et al.; "Effects of temperature and moisture content of the substrate during storage on embryo development and germination in seeds of Musa velutina Wendl. & Drude"; Journal of Horticultural Science and Biotechnology (2008) 83(1):33-36.

Nagano, et al.; "Seed germinability in Musa velutina Wendl & Drude is markedly lowered by 1 week in dry-storage"; Journal of Horticultural Science and Biotechnology (2009) 84(3):325-328.

Nath, Ujjal Kumar et al., Early, non-destructive selection of microspore-derived embryo genotypes in oilseed rape (Brassica napus L.) by molecular markers and oil quality analysis, Mol. Breeding (2007) vol. 19(3):285-289.

Nery, et al.; "Cryopreservation of Anadenanthera colubrina (Vell.) brenan embryonic axes"; Acta Horticulturae (2011)908:227-232.

Neya, et al.; "Ageing increases the sensitivity of neem (Azadirachta indica) seeds to imbibitional stress"; Seed Science Research (2004) 14(2):205-217.

Nogueira, et al.; "Cryopreservation of Byrsonima intermedia A. Juss. embryos using different moisture contents"; Acta Horticulturae (2011) 908:199-202 (2011).

Ntuli, et al.; "Increased Drying Rate Lowers the Critical Water Content for Survival in Embryonic Axes of English Oak (Quercus robur L.) Seeds"; Journal of Integrative Plant Biology (2011) 53(4):270-280; Institute of Botany, Chinese Academy of Sciences (2011).

Obroucheva, et al.; "Vacuolar status and water relations in embryonic axes of recalcitrant aesculus hippocastanum seeds during stratification and early germination"; AoB Plants (2012)12(1).

Ochatt; "Immature seeds and embryos of Medicago truncatula cultured in vitro"; Methods in molecular biology (Clifton, N.J.) (2011) 710:39-52.

Pammenter and Berjak; "Physiology of desiccation-sensitive (recalcitrant) seeds and the implications for cryopreservation"; International Journal of Plant Sciences; (2014) 175(1): 21-28; The University of Chicago, Chicago, IL US.

Percy, et al.; "Desiccation, cryopreservation and water relations parameters of white spruce (Picea glauca) and nterior spruce (Picea glauca x engelmannii complex) somatic embryos"; Tree Physiology (2001) 21(18):1303-1310; Oxford University Press, Oxford, UK.

Plachno and Swiatek; "Unusual embryo structure in viviparous Utricularia nelumbifolia, with remarks on embryo evolution in genus Utricularia"; Protoplasma (2010) 239(1-4):69-80; Springer-Verlag; Berlin/Heidelberg, Germany.

Pond, et al.; "Improving tolerance of somatic embryos of Picea glauca to flash desiccation with a cold treatment (desiccation after cold acclimation)"; In Vitro Cellular and Developmental Biology—Plant (2002) 38(4):334-341; Springer; Germany.

Radha, et al.; "Cryopreservation of excised embryonic axes of Nothapodytes nimmoniana (Graham) Mebberly—A vulnerable medicinal tree species of the Western Ghats"; Indian Journal of Biotechnology (2010) 9(4):435-437.

Rai, et al.; "Effect of ABA and sucrose on germination of encapsulated somatic embryos of guava (Psidium guajava . . . )"; Scientia Horticulturae (2008) 117(3):302-305; Elsevier B.V.; Amsterdam, The Netherlands.

Rai, et al.; "The role of abscisic acid in plant tissue culture: A review of recent progress"; Plant Cell, Tissue and Organ Culture (2011) 106(2):179-190; Springer Science+Business Media B.V.; Berlin/Heidelberg, Germany (2011).

Rajaee, et al.; "Cryopreservation of embryonic axes of Ferula gummosa: A tool for germplasm conservation and germination improvement"; Acta Horticulturae (2012) 964:153-160.

Rakotondranony, et al.; "Seed storage responses in four species of the threatened genus Ravenea (arecaceaer)"; Seed Science and Technology (2006) 34(2):513-517.

Reed and Hummer; "Long-term storage of hazelnut embryonic axes in liquid nitrogen"; Acta Horticulturae (2001) 556:177-180.

Reid and Walker-Simmons; "Group 3 late embryogenesis abundant proteins in desiccation-tolerant seedlings of wheat (Triticum aestivum L.)"; Plant Physiology (1993) 102(1):125-131; American Society of Plant Biologists (ASPB); Rockville, MD US.

Rider, et al.; "Metabolic profiling of the Arabidopsis pkl mutant reveals selective derepression of embryonic traits"; Planta (2004) 219(3):489-499; Springer-Verlag; Berlin/Heidelberg, Germany.

Roschzttardtz, et al.; "Identification of the endodermal vacuole as the iron storage compartment in the Arabidopsis embryo"; Plant Physiology (2009) 151(3):1329-1338; American Society of Plant Biologists; Rockville, MD US.

Sanchez, et al.; "Preservation of Quercus robur germplasm by cryostorage of embryogenic cultures derived from mature trees and RAPD analysis of genetic stability"; Cryo-Letters (2008) 29(6):493-504; CryoLetters, c/o University of Bedfordshire.

Sangtong, et al.; "Serial Extraction of Endosperm Drillings (SEED)—A Method for Detecting Transgenes and Proteins in Single Viable Maize Kernels"; Plant Molecular Biology Reporter (2001) 19(2):151-158.

Santos and Stushnoff; "Desiccation and freezing tolerance of embryonic axes from Citrus sinensis [L.] osb. pretreated with sucrose"; Cryo-Letters (2003) 24(5):281-292.

Schaeffer, et al.; "Segregation for endosperm lysine in F2, F3 and F4 progeny from a cross of in vitro-selected and unselected cultivar of rice"; Theoretical and Applied Genetics (1989) 77(2):176-183; Springer-Verlag; Berlin/Heidelberg, Germany.

Schwienbacher, et al.; "Seed dormancy in alpine species"; Flora: Morphology, Distribution, Functional Ecology of Plants (2011) 206(10):845-856; Elsevier GmbH; Amsterdam, The Netherlands.

(56) References Cited

OTHER PUBLICATIONS

Seran, et al.; "Encapsulation of embryonic axes of *Camellia sinensis* (L.) O. Kuntze (tea) and subsequent in vitro germination"; Journal of Horticultural Science and Biotechnology (2005) 80(1):154-158.
Sharma, et al.; "ABA associated biochemical changes during somatic embryo development in *Camellia sinensis* (L) O. Kuntze"; Journal of Plant Physiology (2004) 161(11)1269-1276; Elsevier GmbH; Amsterdam, The Netherlands.
Sharma, et al.; "In vitro conservation of *Bacopa monnieri* (L.) using mineral oil", Plant Cell Tiss Organ Cult (2012) 111:291-301.
Sopory, et al.; "Early protein synthesis during germination of barley embryos and its relationship to RNA synthesis"; Plant and Cell Physiology (1980) 21(4):649-657; Oxford University Press; Oxford, UK.
Sreedhar, et al.; "In vivo characterization of the effects of abscisic acid and drying protocols associated with the acquisition of desiccation tolerance in alfalfa (*Medicago sativa* L.) Somatic embryos"; Annals of Botany (2002) 89(4):391-400; Annals of Botany Company; Oxford, UK.
Steinmacher, et al.; "Cryopreservation of peach palm zygotic embryos"; Cryo-Letters (2007) 28(1):13-22; CryoLetters, c/o Royal Veterinary College.
Sulusoglu; Development of embryo culture protocol for cherry laurel (*Prunus laurocerasus* L.); Journal of Food, Agriculture and Environment (2012) 10(3-4): 347-352.
Tahir, et al.; "Identification and characterization of PgHZ1, a novel homeodomain leucine-zipper gene isolated from white spruce (Picea glauca) tissue"; Plant Physiology and Biochemistry (2008) 46(12):1031-1039; Elsevier Masson SAS; Oxford, UK.
Vieitez, et al.; "Cryopreservation of zygotic embryonic axes and somatic embryos of European chestnut"; Methods in molecular biology (Clifton, N.J.) (2011) 710:201-213.
Wagner; "Changes in dormancy levels of *Fraxinus excelsior* L. embryos at different stages of morphological and physiological maturity"; Trees—Structure and Function (1996) 10(3):177-182.
Wen, et al.; "Differential responses of Mimusops elengi and Manilkara zapota seeds and embryos to cryopreservation"; In Vitro Cellular and Developmental Biology—Plant (2013) 49(6):717-723; Springer, Germany.
Wesley-Smith, et al.; "Interactions among water content, rapid (nonequilibrium) cooling to -196° C, and survival of embryonic axes of *Aesculus hippocastanum* L. seeds"; Cryobiology (2001) 42(3):196-206; Academic Press.
Withers, "In-vitro conservation", Biological Journal of the Linnean Society (1991) 43:31-42.
Xia and Kermode; "Analyses to determine the role of embryo immaturity in dormancy maintenance of yellow cedar (Chamaecyparis nootkatensis) seeds: Synthesis and accumulation of storage proteins and proteins implicated in desiccation tolerance"; Journal of Experimental Botany (1999) 50(330):107-118; Society for Experiemental Biology; Southhampton, UK.
Xu, et al.; "Abscisic acid and osmoticum prevent germination of developing alfalfa embryos, but only osmoticum maintains the synthesis of developmental proteins"; Planta (1990) 182(3):382-390; Springer-Verlag; Berlin/Heidelberg, Germany.
Zarek; "A practical method for overcoming the dormancy of Taxus baccata isolated embryos under in vitro conditions"; In Vitro Cellular and Developmental Biology—Plant (2007) 43(6):623-630; Springer, Germany.
Zeng et al.; "Cryopreservation study on seeds and embryos in Dalbergia odorifera"; Zhongguo Zhongyao Zazhi (2014) 39(12):2263-2266.
Zhang, et al.; "Optimizing seed water content: Relevance to storage stability and molecular mobility"; Journal of Integrative Plant Biology (2010) 52(3):324-331; 2010 Institute of Botany, Chinese Academy of Sciences.
Zi, et al.; "Proteomics study of rice embryogenesis: Discovery of the embryogenesis-dependent globulins"; Electrophoresis (2012) 33(7):1129-1138; Wiley-VCH Verlag GmbH & Co. KGaA, Weinheim.
International Search Report and Written Opinion of the International Searching Authority for PCT/US2015/034129, dated Aug. 4, 2015.
International Search Report and Written Opinion of the International Searching Authority for PCT/US2015/034145, dated Aug. 27, 2015.
Sylvie Antoine-Michard et al., Spontaneous versus colchicine-induced chromosome doubling in maize anther culture, Plant Cell, Tissue and Organ Culture, 1997, pp. 203-297, vol. 48.
A Kato, Maize Genetics Cooperation Newsletter, 1997. pp. 36-37.
Y Wan et al., Efficient production of doubled haploid plants through colchicine treatment of anther-derived maize callus, Theor Appl Genet, 1989, pp. 889-892, vol. 77.
Y Wan et al., The use of antimicrotubule herbicides for the production of doubled haploid plants from anther-derived maize callus, Theor Appl Genet, 1991, pp. 205-211, vol. 81.
A. T. King et al., Perfluorocarbons and Cell Culture, Biotechnology, Oct. 1989, pp. 1037-1042, vol. 7.
A. H. McKently et al., Agrobacterium-mediated transformation of peanut (*Arachis hypogaea* L.) embryo axes and the development of transgenic plants, Plant Cell Reports, 1995, pp. 699-703, vol. 14.
Takashi Yamakawa et al., Production of Anthocyanins by Vitis Cells in Suspension Culture, Agric. Biol. Chem., 1983, pp. 2185-2191—vol. 47 (10).
Steve Palumbi et al., Simple Fool's Guide to PCR, version 2.0, Oct. 29, 2002, University of Hawaii, pp. 1-45.
Peggy Horn et al., Non-Destructive RAPD Genetic Diagnostics of Microspore-Derived *Brassica* Embryos, Plant Molecular Biology Reporter, 1992, pp. 285-293, vol. 10(3).
International Search Report—PCT/US2015/039449—dated Oct. 7, 2015.
Abdalla and Roberts; "Effects of temperature, moisture, and oxygen on the induction of chromosome damage in seeds of barley, broad beans, and peas during storage"; Annals of Botany (1968) 32(1):119-136; Oxford University Press; Oxford UK.
Adachi, et al.;"Crystal structure of soybean 11S globulin: Glycinin A3B4 homohexamer"; Proceedings of the National Academy of Sciences of the United States of America (2003) 100(12):7395-7400.
Banilas, et al.; "Oleosin di-or tri-meric fusions with GFP undergo correct targeting and provide advantages for recombinant protein production"; Plant Physiology and Biochemistry (2011) 49(2):216-222; Elsevier Masson SAS; Oxford, UK.
Beardmore and Vong, "Role of the cotyledonary tissue in improving low and ultralow temperature to tolerance of butternut (Juglans cinerea) embryonic axes"; Canadian Journal of Forest Research (1998) 28(6):903-910.
Bozorgipour and Snape; "The assessment of in vitro characters and their influence on the success rates of doubled haploid production in barley"; Euphytica (1991) 58(2):137-144; Springer; The Netherlands.
Brownfield, et al.; "Patterns of storage protein and triacylglycerol accumulation during loblolly pine somatic embryo maturation"; Plant Cell, Tissue and Organ Culture (2007) 88(2):217-223; Springer Science+Business Media B.V.; Berlin/Heidelberg, Germany.
Busk and Pages; "Microextraction of Nuclear Proteins from Single Maize Embryos"; Plant Molecular Biology Reporter (1997) 15:371-376; Kluwer Academic Publishers; Belguim.
Capuna, et al.; "Plant regeneration of common ash (*Fraxinus excelsior* L.) by somatic embryogenesis"; In Vitro Cellular and Developmental Biology—Plant (2007) 43(2):101-110; The Society for in Vitro Biology.
Carasso, et al.; "A threatened alpine species, *Fritillaria tubiformis* subsp. moggridgei: Seed morphology and temperature regulation of embryo growth"; Plant Biosystems (2012) 146(1):74-83; Taylor and Francis Group, LLC.
Chia, et al.; "Storage oil breakdown during embryo development of *Brassica napus* (L.)"; Journal of Experimental Botany, (2005) 56(415):1285-1296; Oxford University Press; Southhampton, UK.
Cho, et al.; "Cryopreservation of Citrus aurantifolia seeds and embryonic axes using a desiccation protocol"; Cryo-Letters (2002) 23(5):309-316.

(56) References Cited

OTHER PUBLICATIONS

Corredoira, et al.; "Cryopreservation of zygotic embryo axes and somatic embryos of European chestnut"; Cryo-Letters (2004) 25(1):33-42.
Corredoira, et al.; "Genetic transformation of European chestnut somatic embryos with a native thaumatin-like protein (CsTL1) gene isolated from Castanea sativa seeds" ; Tree Physiology (2012) 32(11):1389-1402; Oxford University Press; Oxford UK.
Crouch and Sussex; "Development and storage-protein synthesis in Brassica napus L. embryos in vivo and in vitro"; Planta (1981) 153(1):64-74; Springer-Verlag; Berlin/Heidelberg, Germany.
Cruz-Cruz, et al.; "Biotechnology and Conservation of Plant Biodiversity", Resources (2013) 2:73-95.
Da Rosa, et al.; "Inhibition of in vitro development of Coffea embryos by exogen caffeine [Inibição do desenvolvimento in vitro de embriões de Coffea por cafeína exógena]"; Revista Brasileira de Sementes (2006) 28 (3):177-184.
Di Nola and Mayer, et al.; "Effect of temperature on glycerol metabolism in membranes and on phospholipases C and D of germinating pea embryos"; Phytochemistry (1986) 25(10):2255-2259.
Dolce, et al.; "Enhanced seed germination of Ilex dumosa R. (Aquifoliaceae) through in vitro culture of cut pyrenes"; HortScience (2011) 46(2):278-281.
El-Sharkawi, et al.; "Trifactorial interactive effects of nutrients, water potential and temperature on carbohydrate allocation to the embryonic axis of desert plant seeds"; Journal of Arid Environments (1997) 35(4):655-664.
Fang, et al.; "Influence of freezable/non-freezable water and sucrose on the viability of Theobroma cacao somatic embryos following desiccation and freezing"; Plant Cell Rep (2009) 28:883-889; Springer; Berlin/Heidelberg, Germany.
Faria, et al.; "Physiological and cytological aspects of Inga vera subsp. affinis embryos during storage"; Brazilian Journal of Plant Physiology (2006) 18(4):503-513.
Farnsworth; "The ecology and physiology of viviparous and recalcitrant seeds"; Annual Review of Ecology and Systematics (2000) 31:107-138.
Fernando, et al.; "Identifying dormancy class and storage behaviour of champak (Magnolia champaca) seeds, an important tropical timber tree"; Journal of the National Science Foundation of Sri Lanka; (2013) 41(2):141-146.
Gifford, et al.; "Control by the embryo axis of the breakdown of storage proteins in the endosperm of germinated castor beanseed: A role for gibberellic acid"; Journal of Experimental Botany, (1984) 35(5):669-677; Oxford University Press; Oxford UK.
Gonzalez-Benito, "Cryopreservation as a tool for preserving genetic variability: Its use with Spanish wild species with possible landscaping value"; Acta Horticulturae (1998) 457:133-142.
Gonzalez-Benito, et al.; "The development of a protocol for the encapsulation-desiccation and in vitro culture of embryonic axes of Quercus suber L. and Q. ilex L."; Silvae Genetica (1999) 48(1):25-28.
Gumilevskaya and Azarkovich; "Physiological and biochemical characteristics of the recalcitrant seeds having dormancy: A review"; Applied Biochemistry and Microbiology (2007) 43(3):332-340; Nauka/Interperiodica.
Hajari, et al.; "A novel means for cryopreservation of germplasm of the recalcitrant-seeded species, Ekebergia capensis"; Cryo-Letters (2011) 32(4):308-316.
Holtman, et al.; "Lipoxygenase-2 oxygenates storage lipids in embryos of germinating barley"; European Journal of Biochemistry (1997) 248(2):452-458.
Hu, et al.; "Seed dormancy in four Tibetan Plateau Vicia species and characterization of physiological changes in response of seeds to environmental factors"; Seed Science Research, (2013) 23(2):133-140; Cambridge University Press; Cambridge UK.

Ipekci and Gozukirmizi; "Direct somatic embryogenesis and synthetic seed production from Paulownia elongata"; Plant Cell Reports (2003) 22(1):16-24; Springer; Berlin/Heidelberg, Germany.
Ishikawa, et al.; "Cryopreservation of zygotic embryos of a Japanese terrestrial orchid (Bletilla striata) by vitrification"; Plant Cell Reports (1997) 16(11):754-757; Springer; Berlin/Heidelberg, Germany.
Jayasanker, et al.; "Low temperature storage of suspension culture-derived grapevine somatic embryos and regeneration of plants"; In Vitro Cellular and Developmental Biology—Plant (2005) 41(6):752-756; Springer, Germany.
Kainer, et al.; "Moist storage of Brazil nut seeds for improved germination and nursery management"; Forest Ecology and Management (1999) 116(1-3):207-217.
Kersulec, et al.; "Physiological behaviour of encapsulated somatic embryos"; Biomaterials, Artificial Cells, and Immobilization Biotechnology (1993) 21(3):375-381.
Kim, et al.; "Cryopreservation of tea (Camellia sinensis L.) seeds and embryonic axes"; Cryo-Letters (2002) 23 (4):209-216.
Kovalchuk, et al.; "Cryopreservation of native kazakhstan apricot (Pr Unus armenia ca L) seeds and embryonic axes"; Cryo-Letters (2014) 35(2):83-89.
Krishna, Kumar and Thomas, "High frequency somatic embryogenesis and synthetic seed production in Clitoria ternatea Linn"; Plant Cell, Tissue and Organ Culture, (2012) 110(1):141-151; Springer Science+Business Media B.V.; Berlin/Heidelberg, Germany.
Kriz; "Characterization of embryo globulins encoded by the Maize glb genes"; Biochemical Genetics (1989) 27 (3-4):239-251; Plenum Publishing Corporation.
Lai and McKersie; "Effect of nutrition of maturation of alfalfa (Medicago sativa L.) somatic embryos"; Plant Science (1993) 91(1):87-95; Elsevier; Oxford, UK.
Lai and McKersie; "Regulation of starch and protein accumulation in alfalfa (Medicago sativa L.) somatic embryos"; Plant Science (1994) 100(2):211-219; Elsevier; Oxford, UK.
Lelu-Walter, et al.; "Simplified and improved somatic embryogenesis for clonal propagation of Pinus pinaster (Ait.)"; Plant Cell Reports (2006) 25(8):767-776; Springer-Verlag; Berlin/Heidelberg, Germany.
Li and Foley; "Cloning and characterization of differentially expressed genes in imbibed dormant and afterripened Avena fatua embryos"; Plant Molecular Biology (1995) 29(4):823-831; Springer, The Netherlands.
Long et al.; "Maturation and germination of Phaseolus vulgaris embryonic axes in culture"; Planta (1981) 153 (5):405-415; Springer-Verlag; Berlin/Heidelberg, Germany.
Lopez-Molina, et al.; "A postgermination developmental arrest checkpoint is mediated by abscisic acid and requires the ABI5 transcription factor in Arabidopsis"; Proceedings of the National Academy of Sciences of the United States of America (2001) 98(8):4782-4787.
Malik, et al.; "Long-term, large scale banking of citrus species embryos: Comparisons between cryopreservation and other seed banking temperatures"; Cryo-Letters (2012) 33(6):453-464.
Maqsood, et al.; "Synthetic seed development and conversion to plantlet in Catharanthus roseus (L.) G. Don."; Biotechnology (2012) 11(1):37-43; Asian Network for Scientific Information.
Martin and Northcote; "Qualitative and quantitative changes in mRNA of castor beans during the initial stages of germination"; Planta (1981) 151(2):189-197; Springer-Verlag; Berlin/Heidelberg, Germany.
Mathieu, et al.; "Cloning of a pine germin-like protein (GLP) gene promoter and analysis of its activity in transgenic tobacco Bright Yellow 2 cells"; Physiologia Plantarum (2003) 117(3):425-434; Munksgaard International Publishers Ltd; Copenhagen, Denmark.
Mieryk; "Seed Proteomics"; Methods in Molecular Biology (2014) 1072:361-377; Springer; Berlin/Heidelberg, Germany.

\* cited by examiner

METHODS AND DEVICES FOR CREATING DOUBLED HAPLOID EMBRYOS USING OIL MATRICES

CROSS REFERENCE TO RELATED APPLICATIONS

This application is a Continuation of U.S. application Ser. No. 14/793,689, filed Jul. 7, 2015, which is a CIP of U.S. National application Ser. No. 14/473,183, filed Aug. 29, 2014, and a CIP of U.S. National application Ser. No. 14/473,114, filed Aug. 29, 2014, which are incorporated by reference in their entirety.

BACKGROUND

Present conventional seed analysis methods used in genetic, biochemical, or phenotypic analysis, require at least a part of the seed to be removed and processed. In removing some seed tissue, various objectives may need to be met. These may include one or more of the following objectives:

(a) maintain seed viability after collection of seed tissue, if required, (b) obtain at least a minimum required amount of tissue, without affecting viability, (c) obtain tissue from a specific location on the seed, often requiring the ability to orient the seed in a specific position, (d) maintain a particular throughput level for efficiency purposes, (e) reduce or virtually eliminate contamination, and (f) allow for the tracking of separate tissues and their correlation to seeds from which the tissues were obtained.

Current conventional seed testing technologies do not address these requirements sufficiently, resulting in pressures on capital and labor resources, and thus illustrate a need in the art to provide seed analysis methods in which the maximum number of objectives is realized. It would also be beneficial if the seed analysis methods could be used in conjunction with other methods in the seed production process.

SUMMARY

Methods for storing, treating and selecting plant embryos are provided herein. Methods for storing genomic DNA and molecular marker assay materials in an oil bilayer for use in high-throughput molecular analysis are also provided. Moreover, methods for treating plant embryos while in an oil matrix are provided, the treatment of which may be chromosome doubling, *Agrobacterium*-mediated transformation, or herbicide selection as part of an embryo rescue process.

In some embodiments, plant embryos may be stored by suspending the plant embryos or plant embryonic tissue in an aqueous solution surrounded by a matrix of one or more oils. Preferably, at least one of the one or more oils has a density greater than that of the aqueous solution. In some aspects, antimicrobial agents and/or minimal growth media may be added to the aqueous solution. In other aspects, the plant embryos or plant embryonic tissue may be stored in cold (preferably 4° C.) and/or dark conditions to prevent premature germination. In some embodiments, the plant embryos or plant embryonic tissue may be transferred for continued storage. In other embodiments, the plant embryos may be transferred to germination medium, and one or more of the plant embryos may be germinated. In still other embodiments, an aliquot of the aqueous solution may be removed, genetic material may be obtained from cellular material in the aliquot, and the genetic material may be used for molecular analysis (e.g. to genotype the stored plant embryos). The molecular analysis may be genotyping, which may occur by way of: single nucleotide polymorphism detection, restriction fragment length polymorphism identification, random amplified polymorphic detection, amplified fragment length polymorphism detection, polymerase chain reaction, DNA sequencing, whole genome sequencing, allele specific oligonucleotide probes, or DNA hybridization to DNA microarrays or beads. In other embodiments, one or more of the steps described above may be automated.

In some embodiments, methods of storing genomic DNA are provided in which genomic DNA, immersed in an aqueous solution, is placed between two oils, one being more dense than water and the other being less dense than water. The genomic DNA in between the oil layers may be stored under light or dark conditions. The genomic DNA in between the oil layers may be stored at a temperature between room temperature and approximately −25 degrees Celsius, or preferably at approximately −20 degrees Celsius. The methods may further comprise removing an aliquot of said genomic DNA as part of an automated process to perform a molecular analysis such as but not limited to genotyping.

In some embodiments, methods of storing molecular marker assay materials, immersed in an aqueous solution, are provided in which genomic DNA is placed between two oils, one being more dense than water and the other being less dense than water. Molecular marker assay materials may comprise primers and probes. The molecular marker assay materials located between the oil layers may be stored under light or dark conditions. The molecular marker assay materials located between the oil layers may be stored at a temperature between room temperature and −25 degrees Celsius. The methods may further comprise removing an aliquot of said molecular marker assay materials as part of an automated process to perform a molecular analysis such as but not limited to genotyping.

In some embodiments, methods of treating plant embryos with a doubling agent are provided. The methods comprise placing doubling media in between two oils, wherein one of the oils is more dense than water and the other is less dense than water; placing one or more plant embryos in the doubling media for 8-48 hours under light conditions; selecting plant embryos; and transferring the selected plant embryos to media for germination or storage. The plant embryos may be haploid. Moreover, an aliquot of the media may be removed, genetic material may be obtained from cellular material in the aliquot, and the genetic material may be used for molecular analysis (e.g. to genotype the treated plant embryos). The molecular analysis may be genotyping, In some embodiments, methods of selecting plant embryos during doubled haploid production are provided. In the methods, (a) doubling media is placed between two oils, in which one of the oils is more dense than water and the other is less dense than water; (b) the plant embryos are placed in the doubling media for 8-48 hours under light conditions, and (c) plant embryos are selected for germination or storage. Between steps (b) and (c), cellular material may be collected from the one or more plant embryos; DNA may be obtained from the cellular material; and genotypic information may be obtained, allowing selection of one or more embryos based on genotypic information. The methods may further comprise transferring the selected plant embryos to media for germination or storage. The doubling media may comprise an anti-microtubule agent. The doubling media may comprise colchicine, pronamide, dithipyr, amiprophosmethyl or trifluralin. The plant embryos placed in the doubling media may be haploid.

In some embodiments, the plant embryos are maize haploid embryos produced by a cross between a male inducer line and a female line of interest, in which the male inducer line contains a marker gene that is expressed in embryo tissue. The marker gene may express anthocyanin pigments, which are only expressed in the diploid embryos. Thus, white embryos that do not express anthocyanin may further be selected for transfer to media for germination or storage. The selection may be performed using a camera or other imaging device. The methods may further comprise germinating or storing the selected embryos.

To facilitate selection of the white embryos, the expression of anthocyanin may be enhanced by aeration of the doubling media or by placing the plant embryos in a hypotonic doubling media comprising perfluorodecalin (PFC).

In some embodiments, methods of transforming plant tissue are provided in which a suspension comprising *Agrobacterium tumefaciens*, which comprises within its genome a recombinant DNA construct comprising one or more genes of interest and a selectable marker gene, between two oils, in which one oil is more dense than water and the other is less dense than water; placing the plant tissue in the suspension; removing the plant tissue from said suspension and cultivating the plant tissue in media; resting the plant tissue in media; and placing the plant tissue in contact with media comprising a selection agent corresponding to the selectable marker gene. The method may further comprise regenerating a plant from said plant tissue, wherein said plant tissue is a plant embryo or plant callus. The plant tissue may be stored in said suspension for up to one hour. Step (d) may comprise resting the plant tissue in media in the dark at a temperature of about 28 degrees Celsius for a period of up to 14 days. The media comprising the selection agent corresponding to the selectable marker gene may be located between two oils, wherein one of the oils is more dense than water and the other is less dense than water.

In some embodiments, methods of incubating plant tissue in a solution comprising a selection agent are provided in which the plant tissue in said solution is located between two oils, wherein one of the oils is more dense than water and the other is less dense than water. The selection agent may be glyphosate, glufosinate, bialaphos, hygromycin B, kanamycin, paromomycin, mannose, phosphinothricin, butafenacil, or R-haloxyfop. The method may further include selecting plant tissue that remains viable following incubation. The plant tissue may be a plant embryo or plant callus.

DETAILED DESCRIPTION

Plant breeding programs can benefit from preservation of viable plant sources, which may include keeping the viable plant sources in a manner that preserves an ability to be grown into a plant as well as keeping the viable plant sources in a manner that prevents germination. One benefit can be seen in that genetic material can be obtained for molecular characterization, allowing selections to be made prior to growing the plant. Additional benefits may include treating haploid plant embryos with chromosome doubling agents while being preserved or transforming viable plant sources while being preserved.

Viable plant sources may be seeds, plant embryos, plant tissue, or whole plants. Most typically, viable plant sources are capable of being grown into plants, although not necessarily. Preservation of seeds typically requires no particular care. When the viable plant sources are embryos, however, special care should be taken to preserve viability.

In one preferred method, plant embryos are suspended in an aqueous solution surrounded by a matrix of one or more oils. Oil having a density less than water will cover the plant embryo(s) in the aqueous solution, while oil having a density greater than water will support the plant embryo(s) in the aqueous solution. In some embodiments, the one or more plant embryos is suspended in an aqueous solution surrounded by a matrix of two or more oils, wherein at least one of the two or more oils is more dense than the aqueous solution and at least one of the two or more oils is less dense than the aqueous solution, further wherein the aqueous solution is surrounded by the oil that is more dense than the aqueous solution and the oil that is less dense than the aqueous solution. In some embodiments, antimicrobial agents and/or minimal growth media may be added to the aqueous solution. In some embodiments, the plant embryos may be stored in cold and/or dark conditions to prevent premature germination. In a preferred embodiment, the plant embryos are stored at a temperature of approximately 4° C. In some embodiments, the plant embryos may be transferred for continued storage. In other embodiments, the plant embryos may be transferred to germination medium, and the plant embryos may be germinated. In a preferred embodiment, an aliquot of the aqueous solution may be removed; genetic material may be obtained from cellular material in the aliquot; and the genetic material may be used for molecular analysis (e.g. to genotype the stored plant embryos).

High density oil that may be used in this method includes but is not limited to perfluoro compounds having 12 compounds (e.g., DuPont's lower viscosity KRYTOX® oils). Low density oil that may be used in this method includes but is not limited to phenylmethylpolysiloxane. Other non-toxic oils known to those of ordinary skill in the art may be used instead of or in combination with these compounds.

Obtaining Genetic Material for Molecular Characterization

In order for genetic material to be analyzed, it must be freed from the cell such that it is accessible for molecular analysis. This may involve physical treatments such as exposure to cold-heat or just heat, incubation with enzymes, or even DNA extraction techniques (although it is important to note that extraction is not a necessary step in obtaining DNA for molecular analysis). Essentially any process that disrupts the tissue and breaks open cells, thereby releasing DNA that can be used for molecular characterization, may be used in the methods provided herein.

In some embodiments, DNA may be obtained from the cellular material by exposing the cellular material to cold-heat or heat, agitating the mixture, and optionally repeating. In other embodiments, DNA may be obtained by incubating cellular material with an enzyme; the enzyme may be VISCOZYME® L, a multi-enzyme complex containing a wide range of carbohydrases, including arabanase, cellulase, β-glucanase, hem icellulase, and xylanase. (See the Sigma Aldrich product catalog). In still other embodiments, obtaining DNA may comprise extraction of the DNA, such as through the use of magnetic particles that bind genetic material or any method known to one of ordinary skill in the art. However, extraction is not necessary for obtaining DNA.

Molecularly Characterizing the Genetic Material from the Multiple Viable Plant Sources In cases where the yield of DNA obtained from embryo tissue is not sufficient for some molecular analysis (e.g. high density genotyping), whole genome amplification techniques may be used. The Qiagen REPLI-g kit, the Sigma-Aldrich SeqPlex kit, or any other technique known to one of ordinary skill in the art may be used to amplify DNA from plant embryonic tissue.

Other useful molecular characterizations may involve sequencing all or part of the genome of the tissue extracted from the seed, or using molecular markers and fluorescent probes to genotype. Molecular characterization need not focus on the genotype of the extracted tissue, but instead may measure other properties such as oil content, oil composition, protein content, or the presence or absence of particular molecules in the tissue.

In a preferred embodiment, genetic material is placed in a well of a multiple well plate containing a bilayer of oil, one layer having a density greater than water and one layer having a density less than water. Multiple wells contain multiple different genetic materials. Fluorescently labeled probes are added to the genetic materials, and thermocycling to cause amplification and hybridization of the probes is performed in the multiple well plate. The wells are irradiated and fluorescence is detected from the labels to generate genotypic data. Alternatively, the genetic material may be sequenced, in whole or in part, in the multiple well plate.

Genomic DNA and/or molecular marker assay materials (such as but not limited to primers and probes) may also be stored in a bilayer of oil to facilitate automation and high-throughput molecular characterization. In both instances, the materials are immersed in an aqueous solution, which is placed between two oils, one being more dense than water and the other being less dense than water. Storage of genomic DNA and/or molecular marker assay materials may be in light or dark conditions and may occur at approximately 4 degrees Celsius or at room temperature. Storage in this manner allows a mechanical device to obtain aliquots from stored genomic DNA and from stored molecular marker assay materials and combine them in a reaction mixture in order to perform high-throughput molecular characterization.

Selecting One or More Viable Plant Sources

In a molecular breeding program, plants or potential plants are selected to participate in subsequent generations based on their genotype. Typically this involves determining whether the plant has inherited one or more desirable traits indicated by genetic markers whose presence or absence can be determined based on the genotyping. Plant breeders select those plants that have the desired traits to participate in further breeding, to inbreed, or as part of a process to create inbreds through haploid doubling techniques. Those plants that are selected based on the presence of desirable traits as determined by their genotype may be grown into mature plants, to obtain haploid material to create a double haploid inbred, to breed with itself to create an inbred, or to breed with other plants to improve and diversify germ plasm.

The plant embryo storage methods described above allow genotypic information to be obtained for plant embryos that are being stored, allowing embryos to be selected based on genotypic information.

The plant embryo storage methods may also be used to treat plant embryos while the plant embryos are stored (short-term or long-term) in an oil matrix.

One treatment may be the doubling of plant embryos with a doubling agent. In the methods, doubling media is placed between two oils, wherein one of the oils is more dense than water and the other is less dense then water; the plant embryos are placed in doubling media for 8-48 hours under light conditions; plant embryos are selected; and the selected plant embryos are transferred to media for germination or storage. The plant embryos may further be germinated or stored. The plant embryos may be haploid. Genetic material may be obtained from the plant embryos and the plant embryos may be molecularly characterized (e.g. genotyping). Selections of the plant embryos may be based on genotypic information.

Methods of chromosome doubling in maize are disclosed in Antoine-Michard, S. et al., *Plant cell, tissue organ cult.*, Cordrecht, the Netherlands, Kluwer Academic Publishers, 1997, 48(3):203-207; Kato, A., *Maize Genetics Cooperation Newsletter* 1997, 36-37; Wan, Y. et al., TAG, 1989, 77: 889-892. Wan, Y. et al., TAG, 1991, 81: 205-211; U.S. Pat. Nos. 8,865,971; and 8,404,930; the disclosures of which are incorporated herein by reference. Typical methods involve contacting the cells with colchicine, anti-microtubule agents or anti-microtubule herbicides, pronamide, nitrous oxide, or any mitotic inhibitor to create homozygous doubled haploid cells. The amount of colchicine used in medium is generally 0.01%-0.2% or approximately 0.05% or APM (5-225 µM). The amount of colchicine can range from approximately 100-600 mg/L, and preferably may be approximately 500 mg/L. The amount of pronamide in medium is approximately 0.5-20 µM. Other agents may be used with the mitotic inhibitors to improve doubling efficiency. Such agents may be dimethyl sulfoxide (DMSO), adjuvants, surfactants, and the like.

In some embodiments, methods of selecting plant embryos during doubled haploid production are provided. In the methods, (a) doubling media is placed between two oils, in which one of the oils is more dense than water and the other is less dense than water; (b) the plant embryos are placed in the doubling media for 8-48 hours under light conditions, and (c) plant embryos are selected. Between steps (b) and (c), cellular material may be collected from the one or more plant embryos; DNA may be obtained from the cellular material; and genotypic information may be obtained, allowing selection of one or more embryos based on genotypic information. The methods may further comprise transferring the selected plant embryos to media for germination or storage and/or germinating the plant embryos. The doubling media may comprise an anti-microtubule agent. The doubling media may comprise colchicine, pronamide, dithipyr, amiprophosmethyl or trifluralin. The plant embryos placed in the doubling media may be haploid.

Maize haploid embryos may be produced by a cross between a male inducer line and a female line of interest, in which the male inducer line contains a marker gene that is expressed in embryo tissue. The marker gene may express anthocyanin pigments, which are only expressed in the diploid embryos. Thus, white embryos that do not express anthocyanin may further be selected for transfer to media for germination or storage. The selection may be performed using a camera or other imaging device.

In the above, expression of anthocyanin (or the observation thereof) may be enhanced by aeration of the doubling media. This may occur by shaking the liquid media prior to contact with the plant embryos or by bubbling filtered air through the three layers (first oil layer, liquid medium, second oil layer) since the phase separation would occur once the air supply is shut down. Another method involves placing the plant embryos in a hypotonic doubling media comprising perfluorodecalin (PFC). The hypotonic doubling media may also comprise bleach to reduce bacterial growth.

The female line of interest may or may not be an inbred and may have a desirable genetic makeup. The female line of interest may also comprise within its genome one or more transgenes of interest.

The haploid inducer lines described herein have incorporated anthocyanin color markers incorporated into their genomes; the markers are expressed both within the kernel pericarp and in the scutellum. The color markers are used to screen the embryos. Haploid embryos lack the paternal gene with the color marker and therefore appear white or colorless.

One of the limitations of using liquid media is that the color marker fails to be expressed when the embryos are submerged in the medium and therefore it is difficult to separate diploids from haploids embryos after doubling. To overcome this limitation, methods to increase dissolved oxygen content within the media may be used to enhance the level of anthocyanin expression or the observation thereof. In methods described herein, anthocyanin expression in liquid media may be enhanced by incubating the embryos in hypotonic liquid media consisting of perfluorodecalin (PFC), a liquid saturated in oxygen, and 0.1% commercial bleach (5% NaOCl v/v), by shaking, and/or by bubbling the medium with filtered air (aeration). Enhancement of anthocyanin expression in liquid media may be performed while the liquid media is located between oils in an oil matrix; however, it is not necessary for the liquid media to be between oils. Selection is facilitated whether or not the liquid media is located between oils in an oil matrix. Moreover, the use of the hypotonic doubling media comprising perfluorodecalin (PFC) to enhance anthocyanin expression is not exclusive to liquid media and may be used to eliminate diploid embryos regardless of how the plant embryos are being stored.

Another treatment may be the transformation of plant tissue with *Agrobacterium tumefaciens*, which has within its genome a recombinant DNA construct that comprises one or more genes of interest and a selectable marker gene. The methods include placing a suspension containing the *Agrobacterium* between two oils, in which one oil is more dense than water and the other is less dense than water; placing the plant tissue in the suspension; removing the plant tissue from the suspension and cultivating the plant tissue in media; resting the plant tissue in the media; and placing the plant tissue in contact with media comprising a selection agent corresponding to the selectable marker gene. The method may further comprise regenerating a plant from said plant tissue, which may be a plant embryo or plant callus. The plant tissue may be stored in the suspension for up to one hour. "Resting" may comprise placing the plant tissue in media in the dark at a temperature of about 28 degrees Celsius for a period of up to 14 days. The media comprising the selection agent may also be located between two oils, wherein one of the oils is more dense than water and the other is less dense than water. However, the step of selecting the embryos can also be performed in media that is not located within an oil matrix.

The benefits to performing *Agrobacterium*-mediated transformation of embryos in an oil matrix are simplification of the downstream multiple culturing process, amenability for automation, a reduction in costs pertaining to consumables, and a reduction in consumable waste.

Another treatment may be the incubation of plant tissue in a solution containing a selection agent. This also may be done while the plant tissue is located between two oils, wherein one of the oils is more dense than water and the other is less dense than water. The selection agent may be glyphosate, glufosinate, bialaphos, hygromycin B, kanamycin, paromomycin, mannose, phosphinothricin, butafenacil, or R-haloxyfop. The method may further include selecting plant tissue that remains viable following incubation. The plant tissue may be a plant embryo or plant callus. This method may be used to determine whether plant tissue includes a native trait that confers the ability to withstand the selection agent.

While the examples provided herein relate to a monocot, specifically maize, those of ordinary skill in the art would understand how to apply the same or similar methods to other monocots and dicots; the methods may be adapted to any plant. For instance, the plant may include but is not limited to maize, soybean, sunflower, sorghum, canola, wheat, alfalfa, cotton, rice, barley, millet, sugar cane, or switchgrass.

Example 1: Embryo Genotyping in Maize

A. Collection of Maize Embryo Material:

Maize embryos were washed 3 times using 2 mL of sterile water. Maize embryos were incubated in a tube containing either 10 µL, 20 µL, 50 µL, 75 µL, or 150 µL of sterile water for either 10 minutes, 20 minutes, or overnight. It was found that adequate genotyping data can be obtained with any of the dilution volumes, and that 10 minutes was a sufficient incubation time. All protocols for washing and incubating the maize embryos were used with all three tissue collection methods described below.

Method 1: The tubes containing the maize embryos were agitated via tapping 10 times and were then spun down in a tabletop centrifuge for 5 seconds. The water was then removed from each tube for analysis. It was found that this method achieved the best results for genotyping.

Method 2: Maize embryos were washed 3 times using 2 mL of sterile water. The maize embryos were incubated in a tube containing 50 µL of sterile water for 10 minutes. The water was then removed from the tube for analysis.

Method 3: Maize embryos were washed 3 times using 2 mL of sterile water. The maize embryos were incubated in a tube containing 50 µL of sterile water for 10 minutes. Tubes containing the maize embryos were agitated via tapping 10 times. The water was then removed from each tube for analysis.

B. Methods to obtain DNA:

Cold-Heat Shock:

Maize embryonic material obtained using all three methods described above was placed in a −80° C. freezer for 20 min; then placed on a thermocycler at 100° C. for 10 min and pipetted up and down to mix. The process was repeated for a total of two rounds. The resulting mixtures were stored at −20° C. It was found that the best results for genotyping were achieved from DNA obtained using this method.

Heat Shock Only:

Maize embryonic tissues were placed on a thermocycler at 100° C. for 10 min and pipetted up and down to mix. The process was repeated for a total of two rounds. The mixtures were stored at −20° C.

Enzymatic Method:

The mixtures from the preceding step were incubated in a 95° C. oven to evaporate off the remaining water. 18.0 μL of PBS solution and 2.0 μL of diluted VISCOZYME® L (commercially available from Sigma-Aldrich; diluted 1:200 in PBS Solution pH 7.4; total vol. 20 μL) were added and the mixtures were incubate at 37° C. for 2 hours. A quantity of 2.0 μL of diluted proteinase K (commercially available from Sigma-Aldrich; diluted 1:20 in PBS Solution pH 7.4) was added and the mixtures were incubated at 55° C. for 50 minutes then heated to 95° C. for 10 min. The mixtures were stored at −20° C.

DNA Extraction:

The mixtures from the methods of Example 1B were incubated in a 95° C. oven to evaporate off the remaining water. 45 μL Lysis buffer PN (LGC Genomics) was added to each mixture, each of which was centrifuged briefly and incubated at 65° C. for 1 hour. To new tubes were added 60 μL Binding buffer PN, 5 μL Sbeadex particles (magnetic particles that bind genetic material, which are commercially available from LGC Genomics) followed by the lysate mixtures, which were then incubated at room temperature for 4 minutes to allow binding of DNA to the particles, vortexed briefly and placed in a magnetic rack to concentrate beads. The lysis buffer was removed and 100 μL wash buffer PN1 (LGC Genomics) was added to resuspend the beads. Washing was repeated using 100 μL wash buffer PN2 (LGC Genomics) followed by a 100 μL pure water wash. 10 μL elution buffer PN was added and the mixtures were incubated at 55° C. for 10 minutes with vortexing every 3 minutes. The magnetic rack was used to concentrate beads and the eluate was transferred to new tubes and stored at −20° C.

C. Whole Genome Amplification

When whole genome amplification was required the following protocol was followed using the REPLI-g®Single Cell Kit (commercially available from Qiagen). Whole genome amplification was done to achieve higher DNA yield and to facilitate the detection of high density marker sets.

2.5 μL template DNA was combined with 2.5 μL Buffer D1 (commercially available from Qiagen; total volume 5.0 μL) and incubated at room temperature for 3 minutes. 5.0 μL Buffer N1 (commercially available from Qiagen; total volume 10.0 μL) was added and the mixtures were vortexed and centrifuged briefly. A Master Mix containing 9.0 μL nuclease-free water, 29.0 μL REPLI-g® Reaction Buffer (commercially available from Qiagen) and 2.0 μL REPLI-g® DNA Polymerase (commercially available from Qiagen) was used per reaction to give 50.0 μL total volume. The mixtures were run on a thermocycler using a 30° C. for 8 hours and 4° C. thereafter. DNA quantitation was performed using a Qubit assay (commercially available from Life Technologies). The DNA product was used directly in the genotyping step.

D. Molecular Analysis

TAQMAN® Marker Analysis

Marker analysis was carried out using TAQMAN® assays (commercially available from Life Technologies). DNA was diluted to a target concentration of 20 ng/μL. A 384 plate containing the DNA was loaded into LC480 real-time PCR thermocycler and run using the following program: pre-incubation: 1 cycle (95° C. for 5 minutes); amplification: 45 cycles, (−95° C. for 30 seconds, −60° C. for 45 seconds (single acquisition), −72° C. for 1 minute (single acquisition); cooling: 1 cycle, (−72° C. for 10 minutes, −40° C. for 30 seconds). Calls were read using Roche LC480 LightCycler® Software (commercially available from Roche Diagnostics).

Results

The foregoing methods all gave acceptable genotyping results.

Example 2: Maize Embryo Storage

Two lines of maize germplasm were selected for testing the impacts of extended embryo storage in an oil matrix on germination rates. Embryos from each line were isolated by hand before being placed into their respective storage condition. All embryos were plated on germination media to evaluate germination rates in a controlled growth chamber. Six embryos of each line were immediately plated on germination media without any storage exposure to act as a control for germination in a controlled growth chamber. Seventy two (72) embryos of each line were isolated and evenly divided across three storage conditions, with a dedicated storage tube for each embryo:

Storage condition 1: 24 embryos were placed in 50 μL aqueous solution surrounded by two layers of oil with significantly different densities, one with a density significantly greater than water and one with a density significantly less than water.

Storage condition 2: 24 embryos were placed in a 50 μL droplet of aqueous solution with an added antimicrobial agent, surrounded by the two oils of condition 1.

Storage condition 3: 24 embryos were placed in a 50 μL droplet of minimal growth media with an added antimicrobial agent, surrounded by the two oils of condition 1.

All tubes were placed in a dark refrigerator at 4 degrees centigrade for the duration of the experiment. At four (4) time points, 6 embryos of each line were removed from their storage condition and plated on germination media in a controlled growth chamber to evaluate germination rates. The time points were as follows:

Time point 1: 15 minutes after placement into storage.
Time point 2: 1 day after placement into storage.
Time point 3: 5 days after placement into storage.
Time point 4: 10 days after placement into storage.

Embryo germination rates were then monitored to determine optimal storage conditions. It was found that germination rates were excellent for embryos stored in each of the three storage methods.

Example 3: Genotyping Reagent Storage Study Methods and Materials

Two components of an endpoint SNP genotyping reaction, genomic DNA and a molecular marker assay (primers and probe), were selected to test the impacts on reagent viability after extended storage in an oil bilayer, at various conditions.

Genomic DNA was isolated from maize leaf tissue and from maize seed tissue via known extraction protocols to evaluate the impact of extended storage, compared to a baseline. A volumetric subset from each tissue type extraction was left at stock extraction concentration and the remaining volume was diluted to a factor well suited for a SNP genotyping reaction. The DNA concentration volumes were further divided to provide dedicated volumes for evaluating storage impacts in Light vs. Dark conditions and Room Temperature vs. 4° Celsius conditions, as well as a combination of each. Four molecular marker assays used for endpoint SNP genotyping of maize were selected to evaluate impact of extended storage, compared to a baseline. A volumetric subset of each molecular marker assay was left at a stock concentration and the remaining volume of each molecular marker assay was diluted to a factor well suited for a SNP genotyping reaction. The molecular marker assay volumes were further divided to provide dedicated volumes for evaluating storage impacts in Light vs. Dark conditions and Room Temperature vs. 4° C. conditions, as well as a combination of each.

Prior to the volume separation steps, a baseline sample was taken from each reagent to generate a baseline data set for comparison at each storage time point. The extracted test DNA reagent was screened against a control molecular marker assay (not the test molecular marker assay) and the test molecular marker assays were screened against control DNA samples (not the test DNA samples). Each reagent volume was placed into an oil bilayer prior to being stored in their respective storage condition (Light/Dark, Room Temp/4° Celsius). At pre-defined time points, aliquots of reagents from each test storage condition, for each reaction component, were taken and screened against control reagent compliments within an endpoint SNP genotyping reaction. Genotypic data from all time points was compared to the baseline for reaction completion efficiency and overall data quality. Data quality from the stored molecular marker assay reagents was comparable to that of the baseline.

Example 4: Haploid Embryo Doubling and Selection in Oil Matrix

Experiments were performed to determine if doubling treatments can be applied to embryos stored in the oil bilayer.

2× colchicine selection media consisting of: 2×DCS Media (Doubling, Colchicine, Sucrose), 2×DCS Media components (per Liter), 300.00 g Sucrose Grade II, 8.67 g of MS Basal Salt Mixture, 0.80 g L-Asparagine Monohydrate, 10.00 mL 36 J Vitamin Solution, 2.50 mL of Thiamine Solution, 0.20 mL of BAP Solution, 1.00 g Colchicine, 41.66 mL of DMSO (20%), and RO water to 1.00 L, was prepared. 2× colchicine selection media was placed in screw-top microcentrifuge tubes and diluted with an equal amount of sterile water to 1× concentration. 50 μL of 1× liquid colchicine selection media was added to each tube, which contained a high-density oil and a low-density encapsulating oil. The colchicine media settles between the oil layers.

Twenty embryos were rescued from an ear produced by a cross between a male inducer line, which comprises in its genome a marker gene that expresses anthocyanin pigments in embryo tissue, and a female line of interest. Embryos were transferred into the colchicine media using a sterilized spatula, and tubes were placed in a lighted growth chamber room for 8-48 hours. Embryos were selected based on the color image from a camera. Purple or diploid embryos were discarded, while the white embryos were transferred to growth media plates. The plates were then placed back in the culture chamber for germination. The germination rate for both haploid and diploid embryos is comparable to the standard protocol without using oil encapsulation.

Example 5: Enhancement of Anthocyanin Expression for Improved Selection

In the methods described in Example 5, the level of anthocyanin expression can be enhanced, resulting in improved selection. Either of the methods described below, as well as other methods known to one of ordinary skill in the art, may be used to increase dissolved oxygen content within the media, thereby enhancing the level of anthocyanin expression or the observation thereof.

In one experiment, the culture media was aerated prior to introducing the embryo into the oil matrix environment. Four mL of culture media in a 50 mL Falcon tube was prepared and placed in a rocker table at maximum speed for several hours. The media was immediately transferred into oil matrix tubes after aeration. The results indicate that the oxygen level in the medium facilitates the detection of anthocyanin coloration for the diploid embryos. Alternatively, liquid medium could also be aerated by bubbling filtered air through the three layers (first oil layer, liquid medium, second oil layer) since the phase separation would occur once the air supply is shut down.

In another experiment, embryos were incubated in a hypotonic liquid medium consisting of PFC (perfluorodecalin; undiluted and in whatever volume needed to cover the embryo) and 0.1% commercial bleach (5% NaOCl v/v). The addition of bleach was sufficient to inhibit bacterial growth without affecting germination when compared to the control. Anthocyanin color appeared at the border of the scutellum within 12 hours of the colchicine treatment and then continued centripetally until the whole embryo became purple-red (if diploid). Germination in liquid medium is statistically similar to the control using solid medium.

Example 6: *Agrobacterium*-mediated Transformation of Maize Embryos in an Oil Matrix An *Agrobacterium* suspension may be prepared (such as shown in U.S. Pat. No. 5,981,840) and then placed between two oils, one of which is more dense than water and the other of which is less dense than water. The *Agrobacterium*-containing suspension would settle between the oil layers.

Embryos are isolated and then placed in the *Agrobacterium*-containing suspension, which is located between the oil layers, for 5 minutes. The embryos are then removed from the *Agrobacterium*-containing suspension and then cultivated for 2-4 days. For the resting step, embryos are transferred to a new plate and incubated in the dark at approximately 28° C. for up to 14 days, in order to eliminate any remaining *Agrobacterium*. For selection, embryos are then placed in contact with media containing a selection agent that corresponds to the selectable marker gene inserted into the vector in the *Agrobacterium*, in order to kill any non-transformation events. The selection step can also take place in media located between two oils in an oil matrix. The transformed cells are then regenerated to form whole plants using tissue culture methods.

The benefit of allowing transformation of the embryo to occur while in media surrounded by the oil bilayer is to simplify the downstream multiple culturing process. The system is more automatable than the conventional methods transferring cultivates using agar based medium and would reduce the cost of consumables as well as the associated waste.

Example 7: Trait Selection of Maize Embryos in Oil Matrix

Effective selection is one of the most critical steps in selecting plants and plant tissues that contain a transgene or native trait of interest. The presence of a selecting agent allows for the proliferation of transgenic tissues and at the same time suppresses or kills untransformed tissue. Similarly, a selecting agent may be used to determine whether a plant tissue includes a native trait that confers the ability to withstand the selection agent. The ideal selection agent should not have a negative impact on subsequent regeneration, rooting and plant growth. Both antibiotics and herbicides can be used as selection agents. Commonly used agents include glyphosate, glufosinate, bialaphos, hygromycin B, kanamycin, paromomycin, mannose, phosphinothricin, butafenacil and R-haloxyfop.

Transformed plant tissue or plant tissue having a resistance trait, such as a plant embryo, can be placed in media comprised of MS salts 4.3 g/l; myo-inositol 0.1 g/l; Thiamine.HCL 0.1 mg/l, Pyridoxine.HCl 0.5 mg/l, Glycine 2.0 mg/l, nicotinic acid 0.5 mg/l and sucrose 40.0 g/l at a pH of 5.6. The selection agent can be added directly to such media and then the media containing the agent, along with the plant tissue, can be located between two oils, wherein one of the oils is more dense than water and the other is less dense than water.

Plant Embryos may be transferred into the selection-containing media using a sterilized spatula, and the embryos in the selection-containing media located between the two oils are placed at 8 degrees C. to 26 degrees C. for up to 7 days for selection. Only embryos that have within their genomes genes that confer tolerance to the selection agent will survive. Image selection based on morphological differences, for example by machine vision and computer processing, may be used to differentiate the viable embryos from the dead embryos.

We claim:

1. A method of treating one or more plant embryos with a doubling agent, said method comprising:
    a. placing doubling media between two oils, wherein one of the oils is more dense than water and the other is less dense than water;
    b. placing one or more plant embryos in the doubling media;
    c. selecting one or more plant embryos; and
    d. transferring the selected plant embryos to media for germination or storage.

2. The method of claim 1, wherein said one or more plant embryos are haploid embryos.

3. The method of claim 1, wherein between steps (c) and (d) cellular material is collected from the one or more plant embryos; DNA is obtained from the cellular material; and genotypic information is obtained from the one or more plant embryos.

4. The method of claim 3, wherein said plant embryos are selected based on genotypic information.

5. A method of selecting one or more plant embryos during doubled haploid production, said method comprising:
    a. placing doubling media between two oils, wherein one of the oils is more dense than water and the other is less dense than water;
    b. placing one or more plant embryos in the doubling media and
    c. selecting one or more plant embryos for germination or storage.

6. The method of claim 5, wherein between steps (b) and (c) cellular material is collected from the one or more plant embryos; DNA is obtained from the cellular material; and genotypic information is obtained from the one or more plant embryos.

7. The method of claim 6, wherein said one or more plant embryos are selected based on genotypic information.

8. The method of claim 7, further comprising transferring the selected plant embryos to media for germination or storage.

9. The method of claim 5, wherein said doubling media comprises an anti-microtubule agent.

10. The method of claim 5, wherein said doubling media comprises colchicine, pronamide, dithipyr, am iprophosmethyl or trifluralin.

11. The method of claim 5, wherein said one or more plant embryos are haploid.

12. The method of claim 5, wherein said one or more plant embryos in step (c) are haploid maize embryos produced by a cross between a male inducer line and a female line of interest.

13. The method of claim 12, wherein said male inducer line contains a marker gene that is expressed in embryo tissue.

14. The method of claim 13, wherein said marker gene expresses anthocyanin pigments.

15. The method of claim 14, wherein plant embryos that are white are selected to be transferred to media for germination or storage.

16. The method of claim 15, wherein selection of the white plant embryos is performed using a camera or other imaging device.

17. The method of claim 15, wherein expression of anthocyanin is enhanced by aeration of the doubling media.

18. The method of claim 15, wherein expression of anthocyanin is enhanced by placing the plant embryos in a hypotonic doubling media comprising perfluorodecalin.

19. The method of claim 15, further comprising germinating or storing the selected plant embryos.

* * * * *